(12) United States Patent
Salmonson

(10) Patent No.: US 7,157,106 B2
(45) Date of Patent: Jan. 2, 2007

(54) TOPICAL ANALGESIC AND METHODS OF USE

(76) Inventor: Roger S. Salmonson, 39 Harvey La., Westborough, MA (US) 01581

( * ) Notice: Subject to any disclaimer, the term of this patent is extended or adjusted under 35 U.S.C. 154(b) by 0 days.

(21) Appl. No.: 10/608,744

(22) Filed: Jun. 27, 2003

(65) Prior Publication Data

US 2005/0100587 A1    May 12, 2005

(51) Int. Cl.
*A10N 65/00* (2006.01)
(52) U.S. Cl. .................. 424/747; 424/746; 424/764; 424/778; 424/736; 514/899; 514/817
(58) Field of Classification Search ................ 424/747, 424/746, 764, 778, 736, 724; 514/899, 939, 514/938, 817
See application file for complete search history.

(56) References Cited

U.S. PATENT DOCUMENTS 5,266,318 A    11/1993    Taylor-McCord
5,650,157 A    7/1997    Bockow
5,968,518 A *  10/1999   Pike
6,548,085 B1*  4/2003    Zobitne et al.

FOREIGN PATENT DOCUMENTS

| JP | 55151514 A | * | 11/1980 |
| JP | 2001139488 A | * | 5/2001 |
| RU | 2027440 C1 | * | 1/1995 |
| RU | 2106875 C1 | * | 3/1998 |

OTHER PUBLICATIONS

Lawless, Julia. The Illustrated Encyclopedia of Essential Oils: The Complete Guide to the Use of Oils in Aromatherapy and Herbalism. Element Books, 1995, USA. pp. 174.*
International Search Report for PCT/US02/10223.

* cited by examiner

*Primary Examiner*—Michele Flood
(74) *Attorney, Agent, or Firm*—Mirick, O'Connell, DeMallie & Lougee LLP

(57) ABSTRACT

Topical analgesics, generally comprising calendula oil and cornmint oil, and methods of use.

2 Claims, No Drawings

TOPICAL ANALGESIC AND METHODS OF USE

CROSS REFERENCE TO RELATED APPLICATION

This application claims priority of patent application Ser. No. 10/113,765, filed on Apr. 1, 2002.

FIELD OF THE INVENTION

This invention relates to topical analgesics and more specifically to topical analgesics that are particularly useful for reducing pain and pain associated with menstrual cramps and methods of use.

BACKGROUND OF THE INVENTION

Topically applied pharmaceuticals, including topical analgesics, are a well known means for administering medicines in a targeted manner by applying the topical directly to the skin at or near the source of the pain or injury. Various formulations are available for a variety of general and specific uses. For example, Bockow, in U.S. Pat. No. 5,650,157, discloses topically applied pharmaceutical compositions comprising marine oils rich in omega-3 fatty acids used in connection with a wide variety of medicinal agents including anti-inflammatory agents, analgesics, vasodilatory agents, anti-pruritic agents, anesthestics, counterirritants, astringents, and astringents, among others. Further, Taylor-McCord, in U.S. Pat. No. 5,266,318, discloses non-ionic therapeutic mixtures comprising aloe vera gel that is useful for treating burns, sores, skin abrasions and other superficial skin ailments. However, there are no currently known topical analgesics that are suitable for reducing pain associated with menstrual cramping.

SUMMARY OF THE INVENTION

It is therefore a primary object of this invention to provide a topical analgesic that reduces underlying pain when applied directly to the skin.

It is a further object of this invention to provide a topical analgesic that is particularly adapted to reduce pain associated with menstruation, and more specifically to reduce menstrual cramping.

The analgesic and methods of the invention were developed as a result of efforts to alleviate chronic pain via topical analgesics and more specifically to develop a topical analgesic for temporary relief from menstrual cramps. The analgesic obviates the need for individuals to ingest systemic, unnecessary multi-symptom medication when the individual is able to identify and topically target areas of bodily pain associated with menstrual cramping.

A preferred formulation of the topical analgesic of the invention generally comprises: 90% calendula oil mixed with 45% of one or more of alcohol, mineral oil glycerin and water; and 10% cornmint oil.

Another preferred formulation of the topical analgesic of the invention generally comprises: an effective amount of each of the following components: cornmint oil; orange oil; pennyroyal oil; rosemary Spanish oil; corianda oil; menthyl acetate; alpha pinene; beta pinene; camphor white oil; calendula oil; mineral oil; and almond oil, wherein said effective amounts are preferably about: 65–66% cornmint, 0.4–1.0% orange oil; 4.0–5.0% pennyroyal oil; 6.0–7.0% rosemary Spanish oil; 0.2–0.4% corianda oil; 1.0–2.0% menthyl acetate; 1.0–2.0% alpha pinene; 0.7–1.5% beta pinene; 5.0–6.0% camphor white oil; 0.04–0.06% calendula oil; 0.02–0.03% mineral oil; and 15.0–16.0% almond oil.

Yet another preferred formulation of the topical analgesic of the invention generally comprises: an effective amount of each of the following components: cornmint oil, orange oil; pennyroyal oil; rosemary Spanish oil; corianda oil; menthyl acetate; alpha pinene; beta pinene; camphor white oil; calendula oil; and mineral oil, wherein said effective amounts are preferably about: 80–81% cornmint oil, 0.4–1.0% orange oil; 4.0–5.0% pennyroyal oil; 6.0–7.0% rosemary Spanish oil; 0.2–0.4% corianda oil; 1.0–2.0% menthyl acetate; 1.0–2.0% alpha pinene; 0.7–1.5% beta pinene; 5.0–6.0% camphor white oil; 0.04–0.06% calendula oil; and 0.02–0.03% mineral oil.

A preferred formulation of the composition of the invention that is particularly suited to reduce pain associated with menstruation, comprising, 90% calendula oil mixed with 45% of one or more of alcohol, mineral oil, glycerin or water; and 10% cornmint oil.

Another preferred formulation of the composition of the invention that is particularly suited to reduce pain associated with menstruation, comprising, an effective amount of each of the following components: cornmint oil; orange oil; pennyroyal oil; rosemary Spanish oil; corianda oil; menthyl acetate; alpha pinene; beta pinene; camphor white oil; calendula oil; mineral oil; and almond oil, wherein said effective amounts are preferably about: 65–66% cornmint, 0.4–1.0% orange oil; 4.0–5.0% pennyroyal oil; 6.0–7.0% rosemary Spanish oil; 0.2–0.4% corianda oil; 1.0–2.0% menthyl acetate; 1.0–2.0% alpha pinene; 0.7–1.5% beta pinene; 5.0–6.0% camphor white oil; 0.04–0.06% calendula oil; 0.02–0.03% mineral oil; and 15.0–16.0% almond oil.

Yet another preferred formulation of the composition of the invention that is particularly suited to reduce pain associated with menstruation, comprising, an effective amount of each of the following components: cornmint oil, orange oil; pennyroyal oil; rosemary Spanish oil; corianda oil; menthyl acetate; alpha pinene; beta pinene; camphor white oil; calendula oil; and mineral oil, wherein said effective amounts are about: 80–81% cornmint oil, 0.4–1.0% orange oil; 4.0–5.0% pennyroyal oil; 6.0–7.0% rosemary Spanish oil; 0.2–0.4% corianda oil; 1.0–2.0% menthyl acetate; 1.0–2.0% alpha pinene; 0.7–1.5% beta pinene; 5.0–6.0% camphor white oil; 0.04–0.06% calendula oil; and 0.02–0.03% mineral oil.

Yet another preferred formulation of the composition that is particularly suited to reduce pain associated with menstruation, comprising, an effective amount of each of the following components: cornmint oil, orange oil; pennyroyal oil; rosemary Spanish oil; corianda oil; menthyl acetate; alpha pinene; beta pinene; camphor white oil; and calendula oil, wherein said effective amounts are preferably about: 80–81% cornmint oil, 0.4–1.0% orange oil; 4.0–5.0% pennyroyal oil; 6.0–7.0% rosemary Spanish oil; 0.2–0.4% corianda oil; 1.0–2.0% menthyl acetate; 1.0–2.0% alpha pinene; 0.7–1.5% beta pinene; 5.0–6.0% camphor white oil; and 0.04–0.06% calendula oil.

A preferred method of the invention for reducing pain associated with menstruation, comprising the steps of: providing a topical analgesic comprising, an effective amount of calendula oil and an effective amount of cornmint oil applying at least one coat of said analgesic directly on skin over one or more areas of pain, wherein said step of applying preferably comprises applying at least 3–4 coats directly on said skin over one or more of said areas of pain; and keeping said areas of pain warm for an effective amount of time. The topical analgesic used in the method may further comprise, an effective amount of components selected from a group consisting of: orange oil; pennyroyal oil; rosemary Spanish oil; corianda oil; menthyl acetate; alpha pinene; beta pinene; camphor white oil; calendula oil; mineral oil; and almond oil.

DETAILED DESCRIPTION OF THE PREFERRED EMBODIMENTS AND METHODS

The topical analgesic of the invention is intended for use as a general topical analgesic, but is especially suited for reducing pain and discomfort associated with menstruation and menstrual cramping. The analgesic and methods of the invention were developed to alleviate chronic pain via topical analgesics and more specifically to provide temporary relief from menstrual cramps. The analgesic is topically applied to enable the individual to identify and target the analgesic to areas where pain exists. As such, individuals do not need to take unwanted and unnecessary multi-symptom oral medications simply to alleviate menstrual cramping. This is particularly important in view of the numerous, undesirable side effects associated with orally administered painkillers. As an added benefit, the analgesic of the invention comprises all naturally existing components.

There are several preferred formulations described herein but each of the formulations comprise calendula oil and cornmint oil in varying concentrations. The calendula oil is of particular active significance to the formulation. Calendula oil has long been recognized as having possible homeopathic uses such as facilitating skin abrasions and burns and as an anti-inflammatory agent, antiseptic, astringent, cholagogue and emmenagogue. However, we have discovered in our efforts to develop the topical analgesic of the invention containing calendula oil has an affirmative effect on nerve axions. Specifically, solutions of the analgesic cause nerve cell axions to retreat. When the analgesic was removed, the axional shape was restored.

Described below are several preferred formulations of the invention.

Formulation 1
  90% calendula oil mixed with 45% of alcohol, mineral oil, glycerin and/or oil; and
  10% cornmint oil.

Formulation 2
  An effective amount of each of the following: cornmint oil; orange oil; pennyroyal oil; rosemary Spanish oil; corianda oil; menthyl acetate; alpha pinene; beta pinene; camphor white oil; calendula oil; mineral oil; and almond oil, wherein said effective amounts are preferably about:
  65–66% cornmint,
  0.4–1.0% orange oil;
  4.0–5.0% pennyroyal oil;
  6.0–7.0% rosemary Spanish oil;
  0.2–0.4% corianda oil;
  1.0–2.0% menthyl acetate;
  1.0–2.0% alpha pinene;
  0.7–1.5% beta pinene;
  5.0–6.0% camphor white oil;
  0.04–0.06% calendula oil;
  0.02–0.03% mineral oil; and
  15.0–16.0% almond oil.

Formulation 3
  An effect amount of each of the following components: cornmint oil, orange oil; pennyroyal oil; rosemary Spanish oil; corianda oil; menthyl acetate; alpha pinene; beta pinene; camphor white oil; calendula oil; and mineral oil, wherein said effective amounts are preferably about:
  80–81% cornmint oil,
  0.4–1.0% orange oil;
  4.0–5.0% pennyroyal oil;
  6.0–7.0% rosemary Spanish oil;
  0.2–0.4% corianda oil;
  1.0–2.0% menthyl acetate;
  1.0–2.0% alpha pinene;
  0.7–1.5% beta pinene;
  5.0–6.0% camphor white oil;
  0.04–0.06% calendula oil; and
  0.02–0.03% mineral oil.

The preferred method of the invention for reducing pain, particularly pain associated with menstruation, comprising the steps of: providing one or more of the topical analgesics of any of the formulations described herein, comprising, an effective amount of calendula oil and an effective amount of cornmint oil; and applying at least one coat of the analgesic directly on skin over one or more areas of pain, wherein said step of applying preferably comprises applying at least 3–4 coats directly on said skin over one or more of said areas of pain; and keeping said areas of pain warm for an effective amount of time.

The analgesic is best applied using an applicator bottle that enables the user to dispense small amounts of the analgesic to targeted areas of the skin. For example, the applicator may comprise a roller ball or an absorbent foam stopper. At the first sign of discomfort or pain, the analgesic is applied directly to the skin over the area of discomfort or pain by rubbing the applicator tip against the skin. The analgesic may be gently massaged into the skin. Three to four coats are preferable, although the effective amount may be varied as needed or desired. The area of application should generally be about as large as the user's hand and will remain moist on the skin for a few minutes after application. Relief is typically obtained in less than ten to fifteen minutes after application. Additional application may be necessary to achieve the desired comfort level.

Although specific features of the invention are described in connection with some of the formulations and methods and not others, this is for convenience only as some feature may be combined with any or all of the other features in accordance with the invention.

Other formulations and methods will occur to those skilled in the art and are within the following claims:

What is claimed is:

1. A composition adapted to reduce pain associated with menstruation, comprising, an effective amount of each of the following components: cornmint oil, orange oil; pennyroyal oil; rosemary Spanish oil; corianda oil; menthyl acetate; alpha pinene; beta pinene; camphor white oil; and calendula oil.

2. The composition of claim 1, wherein said effective amount of each component is about: 80–81% by weight cornmint oil, 0.4–1.0% by weight orange oil; 4.0–5.0% by weight pennyroyal oil; 6.0–7.0% by weight rosemary Spanish oil; 0.2–0.4% by weight corianda oil; 1.0–2.0% by weight menthyl acetate; 1.0–2.0% by weight alpha pinene; 0.7–1.5% by weight beta pinene; 5.0–6.0% by weight camphor white oil; and 0.04–0.06% by weight calendula oil.

* * * * *